(12) United States Patent
Pompeo et al.

(10) Patent No.: US 8,815,776 B2
(45) Date of Patent: Aug. 26, 2014

(54) HERBICIDAL COMPOSITIONS AND METHOD OF USE THEREOF

(71) Applicants: Michael Pompeo, Fayetteville, GA (US); Lawrence A Miller, Brookfield, CT (US); Robert L. Hodge, Sumter, SC (US)

(72) Inventors: Michael Pompeo, Fayetteville, GA (US); Lawrence A Miller, Brookfield, CT (US); Robert L. Hodge, Sumter, SC (US)

(73) Assignee: Proactive, LLC, BrookField, CT (US)

( * ) Notice: Subject to any disclaimer, the term of this patent is extended or adjusted under 35 U.S.C. 154(b) by 0 days.

(21) Appl. No.: 13/726,061

(22) Filed: Dec. 22, 2012

(65) Prior Publication Data

US 2013/0165323 A1    Jun. 27, 2013

Related U.S. Application Data

(60) Provisional application No. 61/579,662, filed on Dec. 23, 2011.

(51) Int. Cl.
*A01N 33/18*    (2006.01)
*A01N 25/04*    (2006.01)

(52) U.S. Cl.
CPC ................ *A01N 25/04* (2013.01); *A01N 33/18* (2013.01)
USPC ........................................................ 504/347

(58) Field of Classification Search
CPC ..................................................... A01N 33/18
See application file for complete search history.

(56) References Cited

U.S. PATENT DOCUMENTS 5,270,286 A * 12/1993 Ong ............................... 504/130
2010/0279865 A1 * 11/2010 Cosky et al. ................... 504/124

* cited by examiner

*Primary Examiner* — Alton Pryor
(74) *Attorney, Agent, or Firm* — Hayden Stone PLLC; Christopher G. Hayden

(57) ABSTRACT

An herbicidal emulsifiable concentrate composition that contains Prodiamine herbicide that shows excellent spreadability and stability and is particularly suitable for effective control of weeds in general residential and commercial landscaped areas.

20 Claims, No Drawings

HERBICIDAL COMPOSITIONS AND METHOD OF USE THEREOF

CROSS-REFERENCE TO RELATED APPLICATIONS

This application claims priority to U.S. Provisional application No. 61/579,662 filed Dec. 23, 2011, titled Herbicidal Compositions and Methods of Use Thereof, the entire document of which is incorporated by reference herein for all allowable purposes.

FIELD OF THE INVENTION

The invention relates to emulsifiable concentrate formulations of prodiamine, and use thereof to control undesired weeds, particularly crabgrass.

BACKGROUND OF THE INVENTION

The statements in this section merely provide background information related to the present disclosure and may not constitute prior art.

Emulsifiable concentrate (EC) formulations are a favored liquid delivery system for agriculturally active compounds. Conventional EC's contain one or more active ingredients dissolved in a water immiscible solvent together with emulsifying surfactants. These solvents typically have very low solubility in water and have a high solubility for most agriculturally active compounds.

The presence of the solvent imparts significant advantages to the formulation, such as a higher degree of systemicity, which leads to higher overall biological activity as compared to other commonly used agricultural formulations such as wettable powders (WP), water dispersible granules (WDG) or suspension concentrates (SC). Such EC's are further easier to transport and store.

A good EC is not made using a simple formula that is transferable from active ingredient to active ingredient. It requires the formation of a stable emulsion upon dilution with water that does not separate upon standing.

Furthermore, there should not be any crystallization of the active compound from the EC after water dilution and the EC itself should be physically and chemically stable during extended storage periods, under wide conditions. It can further incorporate various adjuvants to increase the efficacy of the formulation, that must not disrupt the stability of the emulsion after water dilution.

Some major differential properties that lead to the better efficacy, stability and easier commercial use for EC's versus SC's may be described as; EC's are true solutions vs SC's which are suspensions, EC's are thermodynamically stable vs kinetically stable SC's, EC's have a much smaller particle size (<1 nm vs 2-5 um), the primary stabilization force for EC's is solution energy which is much greater than electrostatic and steric energy for SC's, and the lower intrinsic viscosity of EC's leads to Newtonian flow which is a key factor in non-clogging and even spread of herbicide during commercial sprayings.

Several publications describe the development of herbicidal emulsifiable concentrates, although Prodiamine itself has not been formulated into a commercial emulsifiable concentrate due to it's poor solubility in organic solvents and it's lack of ability to form a stable emulsion in water. More specifically towards the embodiments in the present invention, select publications have attempted to form or improve the emulsion properties of low solubility herbicides such as the dinitroaniline class of compounds, in which prodiamine can be loosely placed. For example, WO 98/48624 shows the improvement of the stability of the EC emulsion by the use of a high amount of a water-insoluble C6-C18 alkyl pyrrolidone. However, these C6-C18 alkyl pyrrolidone compounds are highly corrosive, have significant phytotoxicity and are too expensive for use in many agricultural applications.

U.S. Pat. No. 5,035,741 shows the use of fatty acids in the formulation of emulsifiable concentrates to improve the herbicidal activity of some compounds. U.S. Pat. No. 5,270,286 describes the formulation of a combination of imidazolinone and dinitroaniline herbicides as emulsifiable concentrates with the use of aromatic solvents and alkyl phenol polyethylene oxide condensates to improve solubility.

US20100279865 describes the formulation of a combination of many herbicides with Prodiamine in which ammonium sulfate is used to stabilize the colloidal solution and an oil soluble solvent is specifically excluded, due to the solubilization difficulties inherent in these molecules. US2011281731 describes the formation of an emulsifiable concentrate of dinitroaniline herbicides that avoids crystallization at low temperature and which comprises a diester co-solvent having the following formula R1OOC—(CH2)n—COOR2.

US2005113253 and JP7109193 describe fertilizer compositions that contain Prodiamine but specifically do not describe the potential use of an EC formulation to achieve a superior composition and distributed product. These and other publications in the prior art, describe the inherent difficulty in producing a commercially viable EC formulation and may be instructive for the absence of a commercial EC formulation containing Prodiamine herbicide as the primary active ingredient. Further, none of the above publications provides for a method to produce a stable, low phytotoxic, environmentally friendly emulsifiable concentrate formulation of Prodiamine, which can be used, directly or indirectly, for superior weed control.

SUMMARY OF THE INVENTION

Embodiments of the invention relate to a non-aqueous, emulsifiable concentrate formulation for improved herbicidal protection which consists essentially of
  (a) 5 weight percent to 40 weight percent of Prodiamine active herbicidal ingredient;
  (b) 20 weight percent to 80 weight percent of a solvent selected from fatty acid dialkylamide solvent, where the alkyl is C1-C6, preferably C1-C3 alkyl groups, and the fatty acid is C10-C24, typically C12-C18, dimethylsulfoxide, an alkyll pyrrolidinone, preferably N,methylpyrrolidinone; gamma butyrolactone
  (d) 1 weight percent to about 12 weight percent of an alkyl-alkoxylate-based emulsifier, typically a alkyl-based EO-containing block copolymer emulsifier, for example an Ethylene oxide/Propylene oxide alkyl (e.g., butyl) block copolymer;
  (e) 0.5 weight percent to 12 weight percent of a hydrophilic non-ionic emulsifier, typically a ethoxylated fatty alcohol or polyalcohol, for example a tridecyl alcohol hydrophilic non-ionic emulsifier; and
  (f) optionally 0.1 up to 8 weight percent of an anionic emulsifier, for example a fatty acid benzene solfonate, particularly calcium salts of dodecylbenzenesulfonate.

The EC must be shelf stable, for example for at least six months, and must form a commercially acceptably stable emulsion on mixing with water. The use of NMP allows the formulation to be prepared with lower solvent concentrations, as NMP has at least twice the solvating capacity of the other solvent, Embodiments of the invention relate to a non-aqueous, emulsifiable concentrate formulation for improved herbicidal protection which consists essentially of
(a) 10 weight percent to 40 weight percent of Prodiamine active herbicidal ingredient;
(b) optionally 1 weight percent to 60 weight percent of a fatty acid dialkylamide solvent;
(c) 5 weight percent to 50 weight percent of a polar aprotic organic solvent, for example wherein the polar aprotic organic solvent consists of, consists essentially of, or comprises N,M-pyrrolidinone;
(d) 1 weight percent to 12 weight percent of an alkyl-alkoxylate-based emulsifier, typically a alkyl-based EO-containing block copolymer emulsifier, for example an Ethylene oxide/Propylene oxide alkyl (e.g., butyl) block copolymer;
(e) 0.5 weight percent to 5 weight percent of a hydrophilic non-ionic emulsifier, typically a ethoxylated fatty alcohol, for example a tridecyl alcohol hydrophilic non-ionic emulsifier; and
(f) optionally, up to 5 weight percent of an anionic emulsifier, for example a fatty acid benzene solfonate, particularly calcium salts of dodecylbenzenesulfonate.

Prodiamine is a selective herbicide having a formula N3,N3-di-n-propyl-2,4-dinitro-6-(trifluoromethyl)-m-phenylenediamine. Prodiamine is typically used as a pre-emergence herbicide for season long control of grass and broadleaf weeds, including crabgrass. Prodiamine is typically used at application rates of between 0.28 and 2.8 kg/ha for effective pre-emergence weed control. An emulsifiable concentrate consists of a herbicide dissolved in an organic solvent, with sufficient emulsifier added to create a stable oil-in-water emulsion. There are no emulsifiable concentrate formulations of prodiamine commercially available. Emulsifiable concentrates are more effective than are comparable suspension concentrates.

One important aspect of preparing an EC of prodiamine having greater than 10% active ingredients, and especially greater than 20% active ingredients, is solubilizing the active ingredient. It is easier to formulate a emulsifiable concentrate ("EC") having a few percent or less prodiamine, but the industry demands more concentrated products to reduce shipping aqnd storage costs, as well as packaging costs. We found alkyl pyrrolidinones, particulary N-methylpyrrolidinone ("NMP"), to be particularly useful to formulate a high-concentration prodiamine EC, that is, greater than 10% by weight active ingredient. Dimethylsulfoxide is useful, but has less than half the solubilizing ability as NMP. Use of DMSO in the absence of NPM will result in a practical limitation of less than 10% prodiamine in the EC. Other solubilizing solvents include fatty acid amide solvents such as N,N-dimethylcaprylamide (Cognis Agnique KE-3658) and N,N-dimethyloctanamide (Halcomid M8-10). These solvents are "green," but use in the absence of NPM will result in a practical limitation of less than about 10% prodiamine.

The invention also relates to the use of such an emulsifiable concentrate composition as a herbicide. Polar organic solvents such as N-methypyrrolidone (NMP), dimethylformamide (DMF) and dimethylsulfoxide (DMSO) have been used to impart good solubility properties to a number of organic compounds but show environmental and phytotoxicity necessitating their reduction in formulations. Surprisingly, gamma-Butyrolactone also also shows solvating capacity near that of DMSO and the fatty amide solvents. Dimethylacetamide is expected to have good solvating properties but was not tested. Dimethylformamide is also expected to have good solvating properties but use is highly restricted.

Accordingly, it is an object of the present invention to produce a stable, low phytotoxic EC concentrate formulation of prodiamine. We believe a EC utilizing one or more fatty amide solvents, e.g. an optionally alkylated C8 to C18 fatty amide, gamma-Butyrolactone, DMSO, or combination can provide a formulated EC with an acceptable amount of prodiamine, say 5% to 15%. NMP (CAS 872-50-4) provides superior solvating capacity, more than twice other solvents tested. We believe that treatment at label rates of 0.3 to 0.5 pounds active ingredient per acre can be achieved using NMP as the primary solvent in the EC formulation.

The presence of NMP in combination with fatty acid amides, for example 1 to 3 parts fatty acid amides per part NMP, did not show phytotoxicity, even at application rates substantially in excess of label rates.

Embodiments of the invention relate to a non-aqueous, emulsifiable concentrate formulation for improved herbicidal protection which consists essentially of
(a) 10 weight percent to 30 weight percent of Prodiamine active herbicidal ingredient
(b) 30 weight percent to 60 weight percent of a fatty acid dialkylamide solvent
(c) 10 weight percent to 30 weight percent of a polar aprotic organic solvent
(d) 5 weight percent to 8 weight percent of an alkyl based block copolymer emulsifier
(e) 2 weight percent to 5 weight percent of an trialkyl alcohol hydrophilic non-ionic emulsifier
(f) optionally, up to 2 weight percent of an anionic emulsifier, and to the use of such an emulsifiable concentrate composition as a herbicide.

Embodiments of the invention also relate to a non-aqueous, emulsifiable concentrate formulation for improved herbicidal protection which do not contain alkyl pyrrilodinones, for example an EC which consists essentially of
(a) 10 weight percent to 30 weight percent of Prodiamine active herbicidal ingredient;
(b) 30 weight percent to 60 weight percent of a fatty acid dialkylamide solvent;
(c) 10 weight percent to 30 weight percent of a polar aprotic organic solvent selected from DMSO and gamma-Butyrolactone;
(d) 2 weight percent to 8 weight percent of an alkyl based block copolymer emulsifier;
(e) 2 weight percent to 8 weight percent of an trialkyl alcohol hydrophilic non-ionic emulsifier; and
(f) optionally, up to 2 weight percent of an anionic emulsifier.

A preferred embodiment of the invention is a non-aqueous, emulsifiable concentrate formulation for improved herbicidal protection which consists essentially of
(a) 15 weight percent to 40 weight percent, preferably 20 to 30 weight percent, of Prodiamine active herbicidal ingredient;
(b) 20 weight percent to about 50, for example 25 to 45, weight percent of N,M-pyrrolidinone;
(c) optionally 1 weight percent to 50, for example 5 to 30 weight percent, of a fatty acid dialkylamide solvent;
(d) 2 weight percent to 6 weight percent of an alkyl based block copolymer emulsifier;
(e) 1 weight percent to 5 weight percent of an trialkyl alcohol hydrophilic non-ionic emulsifier;
(f) 0.1 to 2 weight percent of an anionic emulsifier such as a alkyl sulfonate or alkyl aryl sulfonate. This latter embodiment, having greater concentrations of has an ability to carry more prodiamine.

A preferred embodiment of the invention is a non-aqueous, emulsifiable concentrate formulation for improved herbicidal protection which consists essentially of
(a) 15 weight percent to 20 weight percent of Prodiamine active herbicidal ingredient;
(b) 25 to about 35 weight percent of N,M-pyrrolidinone;
(c) optionally 40 to 50 weight percent, of a fatty acid dialkylamide solvent;
(d) 2 weight percent to 6 weight percent of an alkyl based block copolymer emulsifier;
(e) 1 weight percent to 5 weight percent of an hydrophilic non-ionic emulsifier such as a an ethoxylated fatty alcohol, for example an ethoxylated isotridecylalcohols;
(f) 0.1 to 2 weight percent of an anionic emulsifier such as an alkyl sulfonate or alkyl aryl sulfonate. This embodiment showed excellent stability, excellent efficacy, and very little phytotoxicity.

Generally, the term "consists essentially of" means there are no other herbicidal active ingredients in the EC.

The more consistent application of active ingredient present in an emulsifiable concentrate can provide for better pre-emergent efficacy. Such EC's when applied to granular carriers like fertilizer or cob can be expected to provide better coverage and effectiveness resulting in the potential lowering of herbicide loading on the environment.

It is a further object of this invention to provide methods for controlling undesired weeds, by application to plants, of a herbicidally effective amount of the said EC formulation upon dilution with water. Yet another object of this invention is to provide a method to extend the application range and reduce the number of spraying for seasonal control of weeds such as crabgrass by the use of said EC formulation in general residential and commercial landscaped areas.

Another objective of this invention is to provide a method to spray on a formulation of Prodiamine onto urea and other fertilizer granules and achieve superior spreadability and distribution of the active herbicide than achievable by the use of SC or physical mixing with Water Dispersible Granule formulations of Prodiamine. These and other objects and features of the invention will be more apparent from the detailed description set forth herein below, and from the appended claims.

Embodiments of the invention relate to a non-aqueous, emulsifiable concentrate formulation for improved herbicidal protection which consists essentially of:
(a) 5 weight percent to 20 weight percent of Prodiamine active herbicidal ingredient;
(b) 30 weight percent to 60 weight percent of a fatty acid dialkylamide solvent;
(c) optionally 10 weight percent to 30 weight percent of a polar aprotic organic solvent
(d) 5 weight percent to 8 weight percent of an alkyl based block copolymer emulsifier
(e) 2 weight percent to 5 weight percent of an trialkyl alcohol hydrophilic non-ionic emulsifier
(f) optionally, up to 2 weight percent of an anionic emulsifier, and to the use of such an emulsifiable concentrate composition as a herbicide.

Further areas of applicability of the present teachings will become apparent from the description provided herein. It should be understood that the description and specific examples are intended for purposes of illustration only and are not intended to limit the scope of the present teachings.

DETAILED DESCRIPTION OF THE INVENTION

The following description is merely exemplary in nature and is not intended to limit the present disclosure, application, claims, compositions, or uses. While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

All percentages and the term "w/w" used herein unless specifically stated are percent by weight, and all component amounts recited as "parts" are parts by weight and are usually on a basis of parts per part of the active ingredient. The term "ppm" is parts per million by weight. When salts of components are mentioned, unless otherwise specifically stated, the composition can contain the acid form of the component, one or more salts of the component, or any mixture thereof.

The aprotic solvent is preferably a pyrrolidone such as NMP, though one or more of dimethylsulfoxide (DMSO), dimethylformamide, and gamma-Butyrolactone alone or in mixtures, including mixtures with NMP, are useful. DMSO and gamma-Butyrolactone dissolve 0.24 to 0.25 grams prodiamine per gram solvent. NMP dissolves 0.68 grams prodiamine per gram solvent. The aprotic solvent is the primary solvent in most embodiments of the EC.

There are a number of solvents that are not suitable and would be included only to change the composition. Examples, and solubility of prodiamine in grams AI per gram solvent, are shown below for completeness.

| Trade Name | Description | Solubility, g prodiamine/ g solvent |
| --- | --- | --- |
| Aromatic 150 | Aromatic Hydrocarbon | 0.080 |
| Aromatic 200 | Aromatic Hydrocarbon | 0.070 |
| Glycol Ether EB | Diethylene glycol monobutyl ether | 0.020 |
| Carbitol TM | Diethylene glycol monomethyl ether | 0.010 |
| Jefsol 1555 | Proprietary Solvent (Carbonate) | 0.004 |
| Glycol DPM | Dipropylene glycol methyl ether | 0.008 |
| DEGEE | Diethylene glycol monoethyl ether | 0.050 |

Fatty amides, also called "fatty acid solvents" in this application, are amides formed from a fatty acid and an amine, of which many are known. Preferred are di-substituted fatty acid amides, which include as non-limiting examples N,N-dimethylcaprylamide (available from Cognis as Agnique™ KE-3658), and N,N-diethyloctanamide (available as Halcomid™ M8-10). These compounds can fully or partially replace aprotic solvents, and the solvating capacity approaches that of less-preferred aprotic solvents such as DMSO and gamma-Butyrolactone, that is, 0.24 to 0.25 grams prodiamine per gram solvent. A mixture of C8 and C10 fatty acid dimethylamide, (CAS 1118-92-9 and 14433-76-2) are useful.

The alkyl-alkoxylate-based emulsifier is typically an alkyl-based EO/PO-containing block copolymer emulsifier, for example an Ethylene oxide/Propylene oxide alkyl (e.g., butyl) block copolymer. It is possible to use suitable co-polymers of ethylene oxide and propylene oxide, such as ABA or BAB block copolymer or BA block copolymers. The alkyl group can range from C3 to C7, for example. A preferred group of ethylene oxide/propylene oxide block copolymers for use in the compositions of this invention are butyl based poly(oxypropylene)poly(oxyethylene) block copolymers having an average molecular weight in a range of 2,400 to 3,500 (e.g. TOXIMUL™ 8320, Stepan Chemical Co.) Also useful is Harcros™ TDA-12.

The hydrophilic non-ionic emulsifier can be a ethoxylated alcohol. A C9 to C18 alcohol can be used, with for example 8 to 20 EO units, for example a tridecyl alcohol hydrophilic non-ionic emulsifier. Examples include Makon™ TD-12, a tridecyl alcohol ethoxylate, POE-12 available from Stepan, or Harcros TDA-12.

Generally an anionic emulsifier can provide added emulsion stability, and alkyl sulfonates are useful for this purpose, for example a fatty acid benzene sulfonate, particularly calcium salts of dodecylbenzenesulfonate.

EXAMPLES

The following examples are provided for illustrative purposes only and are not limiting to this disclosure in any way. Indeed, various modifications of the invention, in addition to those shown and described herein, will become apparent to those skilled in the art from the following examples and the foregoing description. Such modifications are also intended to fall within the scope of the appended claims.

A first prodiamine EC composition #1 is shown in Table 1 below.

TABLE 1

Prodiamine 2 EC Composition 1

| INGREDIENT | Concentration, w/w | Upper limit | Lower limit |
|---|---|---|---|
| Prodiamine Technical (96%) | 26.3 | 27.09 | 25.51 |
| N,N-dimethylcaprylamide | 46 | 47.38 | 44.62 |
| N-methylpyrrolidone | 20.7 | 21.32 | 20.08 |
| EO-PO butyl block copolymer | 3.15 | 3.31 | 3 |
| Tridecyl alcohol | 2.45 | 2.57 | 2.33 |
| Calcium dodecylbenzenesulfonate, 60% linear | 1.4 | 1.47 | 1.33 |

The above composition was stable and dispersed readily when admixed with water.

A second prodiamine EC composition #2 is shown in Table 2 below.

| INGREDIENT | Purpose | Concentration, w/w |
|---|---|---|
| Prodiamine Tech (96%) | Active Ingredient | 30 |
| N,N-diethyloctanamide | Fatty amide solvent | 50 |
| N,N-dimethylformamide | Aprotic solvent | 12 |
| n-butanol alkoxylate | alkyl-based copolymer emulsifier | 5 |
| Tridecyl alcohol EO | Hydrophilic non-ionic emulsifier | 2 |
| Calcium dodecylbenzenesulfonate, 60% linear | | 1 |

This EC was stable and dispersible, but was not preferred due to the use of dimethylformamide.

A third prodiamine EC composition #3 is shown in Table 3 below.

| INGREDIENT | Purpose | Concentration, w/w |
|---|---|---|
| Prodiamine Tech (99.1%) | Active Ingredient | 25.45 |
| N,N-diethyloctanamide | Fatty amide solvent | 46.6 |
| NMP | Aprotic solvent | 20.95 |
| Butyl- PO/EO block copolymer | Emulsifier | 3.15 |
| Ethoxylated alcohol | Surfactant | 2.45 |
| Calcium alkylbenzene sulfonate | Emulsifier | 1.40 |

This EC was stable and dispersible, and is a preferred formulation.

Various embodiments of the formulations disclosed herein, when formulated into a herbicidal composition, show a surprising and unexpected performance in efficacy and low phytotoxicity for general residential and commercial landscaped herbicide treatment as well as for direct application to urea and other fertilizers for superior pre-emergence weed control.

To demonstrate this activity, a series of trials were performed and are described below.

Field Test 1 Objective was to evaluate Example 1 (Table 1) formulation efficacy on pre-emerge crabgrass (*Digitaria ischaemum*) against market standard(s) in LaTour, Mo. Other products tested were Barricade 4L at 22 fl. Oz./acre (0.68 lb prodiamine/acre), Dimension 40WP at 0.6 lb./acre (0.24 lb Dithiopyr/acre), and Example 1 at 43.56 fl. Oz. per acre (0.68 lb. prodiamine/acre). Test data, percent crabgrass in stand at 58 and 100 days after treatment, are shown below. The differences between treatments were not statistically significant.
Barricade 4L at 22 fl. Oz./acre (0.68 lb prodiamine/acre): June 5, 2%, and July 17, 39%
Dimension 40WP at 0.6 lb./acre (0.24 lb Dithiopyr/acre): June 5, 2%, and July 17, 32%
Example 1 at 43.56 fl. Oz./acre (0.68 lb. prodiamine/acre): June 5, 2%, and July 17, 43%
Untreated, June 5, 54%, and July 17, 99%.

Field test #2, to compare Barricade to Example 1 Prodiamine 2 EC for turfgrass safety. 3×log study on bluegrass *Poa pratensis* in LaTour, Mo. Treatments were applied with an application volume of 43.56 gallons per acre as a foliar spray. Active ingredients were logged at ¼ steps with a reduction in AI by 25% from the previous step. Data at 3, 7, and 14 days after treatment are below, with damage on a scale of 0-9.
Barricade 4L at 90 fl. Oz./acre (2.8 lb prodiamine/acre):
3 DAT damage 1, 7 DAT damage 1, 14 DAT damage 0.
Example 1 at 144 fl. Oz./acre (2.25 lb prodiamine/acre):
DAT damage 1, 7 DAT damage 0, 14 DAT damage 0.

Field test #2 showed no phytotoxicity was observed Barricade 4FL, and for Example 1 (Prodiamine 2EC) at 3DAT only slightly phytotoxic at Step 1 and 2 application rates. Step 1 was slightly phytotoxic at 7DAT and no phytotoxicity at 14DAT.

Field test #3 was to compare Barricade to experimental Prodiamine 2 EC for turfgrass safety. A 3×log study was done on tall fescue (*Festuca arundinacea*) in LaTour, Mo. Treatments were applied with an application volume of 43.56 gallons per acre via foliar spray. Active ingredients were logged at ¼ steps with a reduction in AI by 25% from the previous step. Step 1 is the starting full AI load rate followed by a 25% AI reduction from the previous step through step 6. Initial application was 72 fl. Oz. Barricade 4FL per acre (2.25 lb prodiamine/A), and Example 1 (Prodiamine 2EC) was applied at 115 fl. Oz. per acre (1.8 lb/A). Conclusion: For Barricade 4FL no phytotoxicity was observed, and for Prodiamine 2EC at the high rate (step 1) only slight visual phytotoxicity was observed throughout the study.

A stable prodiamine EC formulation called PA-1010 is shown in Table 4 below:

TABLE 4

| Ingredients | % By Wt. |
|---|---|
| Prodiamine Tech (99.36% A.I.) | 15.3% |
| Agnique ™ KE 3658 fatty acid amide solvent | 47.8% |
| Mpyrol ™ N-methylpyrrilidinone | 30.0% |

TABLE 4-continued

| Ingredients | % By Wt. |
|---|---|
| Toximul ™ 8320 butyl based poly(oxypropylene)poly(oxyethylene) block copolymers | 3.0% |
| Agnique ™ TDA-12 Ethoxylated Isotridecylalcohols (CAS 78330-21-9) | 2.45% |
| Ninate 60 L Calcium alkylbenzene sulfonate | 1.4% |

This sample PA-1010 was clear and had excellent stability and emulsion, and was the subject of field tests described below.

Field test 1-2012 evaluated turfgrass phytotoxicity using the Example 4 (Table 4) formulation. The test was performed by Virginia Tech University (Blacksburg, Va.), TEST #63-12, on Kentucky bluegrass (Midnight) at 0.6" fairway mowing height in an irrigated site with irrigation received as needed. The grass was treated May 29, 2012. No injury to Midnight Ky bluegrass observed throughout the study (28 days). No significant differences in % turfgrass cover were noted compared to the untreated control 28 days after the test was initiated. PA-1010 was applied at 40 fl. Oz. per acre.

|  |  |  |  | % Turfgrass Cover | |
|---|---|---|---|---|---|
| Days After Application (DA-A) | 9 | 17 | 28 | 0 | 28 |
| PA-1010 |  |  |  |  |  |
| Turfgrass Injury (%) | 0 | 0 | 0 |  |  |
| % Turfgrass Cover |  |  |  | 71.3 | 61.3 |
| Untreated |  |  |  |  |  |
| Turfgrass Injury (%) | 0 | 0 | 0 |  |  |
| % Turfgrass Cover |  |  |  | 77.5 | 68.8 |

There was no statistically significant difference between the treated blocks and the control.

Field test 2-2012 evaluated turfgrass phytotoxicity using the Example 4 (Table 4) formulation. The test was performed by Virginia Tech University (Blacksburg, Va.), TEST #64-12, on Perennial ryegrass (ASP6004) at 0.6" fairway mowing height in an irrigated site with irrigation received as needed. The grass was treated May 29, 2012. PA-1010 was applied at 40 fl. Oz. per acre. No injury to Perennial ryegrass observed throughout the study (28 days). No significant differences in % turfgrass cover were noted compared to the untreated control 28 days after the test was initiated.

|  |  |  |  | % Turfgrass Cover | |
|---|---|---|---|---|---|
| Days After Application (DA-A) | 10 | 17 | 28 | 0 | 28 |
| PA-1010 |  |  |  |  |  |
| Turfgrass Injury (%) | 0 | 0 | 0 |  |  |
| % Turfgrass Cover |  |  |  | 72.5 | 65 |
| Untreated |  |  |  |  |  |
| Turfgrass Injury (%) | 0 | 0 | 0 |  |  |
| % Turfgrass Cover |  |  |  | 72.5 | 63.8 |

There was no statistically significant difference between the treated blocks and the control.

Field test 3-2012 was conducted to test if application of PA-1010 results in phytotoxicity to desired cool season turfgrasses. The turf species tested was Kentucky bluegrass (*Poa pratensis*) that had a small amount of perennial ryegrass (*Lolium perenne*). The study was conducted at The Ohio Turfgrass Foundation Research and Education Center in Columbus, Ohio. The sites of the experiment was weed-free. Individual treatment plots were 3×6 ft and there were treatments and an untreated control (Table 1). The experimental design was a randomized complete block with 3 replications. The experiments were all established on Jun. 5, 2012. Pa-1010 was applied at 40 fl oz per acre. A backpack carbon dioxide sprayer equipped with 6503 nozzles with a spray pressure of 40 psi was used to apply the products with the equivalent of 2 gal $H_2O/1000$ $ft^2$. Turfgrass phytotoxicity data were collected at 7, 14, and 28 days after application of treatments (DAT) by visually estimating percent injury to the turfgrass on a scale of 0 to 10 with 0=no injury and 10=dead turfgrass. The data were analyzed using the General Linear Models procedure of SAS. Fishers protected LSD was conducted on the data.

Barely noticeable injury symptoms were noted in all treated plots at 7 DAT (Table 1). This was primarily a very light chlorosis. However, none of the differences were statistically significant. The rates tested caused no injury significantly different than the untreated plots at 14 DAT. At 28 DAT no phytotoxicity was noted. Finally, though the rating for plots treated with treatment 4 was numerically lower, there were no significant quality differences observed at 43 DAT. PA-1010 was safe to Kentucky bluegrass at all rates tested. Treated and control blocks showed 0.3 damage at day 7 and 0.0 damage at days 14 and 28, where zero is no damage and 10 is dead turf Turf quality for both treated and untreated was rated 7.0 at 43 days after testing.

Field test 4-2012 performed at Southeastern Turfgrass Research & Consulting, LLC (Lexington, Ky.) to evaluate phytotoxicity on a stand of well-managed lawn-height tall fescue turf Tall fescue (Barrington/Barlexas/Barvado tall fescue blend by Barenbrug) at 3.5" lawn mowing height was treated on Jul. 23, 2012. PA-1010 was applied at 40 fl. Oz. per acre. No phytotoxicity was observed at any rating period. Turfgrass quality, where 1=brown, dead turf and 9=perfect green turf, was 6.5 for the treated plots at day 6 versus 6.8 for untreated control. At days 20 and 26 after treatment, turfgrass quality was identical between treated and untreated blocks, measuring 7.0 in all cases.

Field test 5-2012 by Southeastern Turfgrass Research & Consulting, LLC evaluated phytotoxicity at a field between a pond and trees in Lexington, Ky. Tall fescue at 3.5 inches was in 44 Sand, 48% silt, 8% clay, OM: 3.9 Loam with a CEC of 9.4 and a pH of 6.1. Fertilizer level was poor. Appliccation was by CO2 sprayer at 30 psi, applying 40 fl. Oz. per acre of PA-1010 on May 24, 2012. The test showed minor differences in turf quality at day 15 between treated and untreated, and results were identical between treated and untreated on days 21 and 28 after treatment.

Field test 6-2012 was conducted at the Landscape Horticulture Research Center at the University Of Illinois¬-Urbana/Champaign in Urbana, Ill. Treatments were applied to a mature stand of Kentucky bluegrass L.cv. 'Bewitched' maintained at a 0.875-inch height of cut. The experimental design used was a randomized complete block with four replications and plots measured 4×6 feet. Treatments were applied with a backpack-type CO2 sprayer at 32PSI fitted with VS8002 nozzles (TeeJet Technologies, Wheaton, Ill.) and a spray volume of 50 gallons acre-1. Treatments were applied on Jun. 27, 2012. PA-1010 was applied at 40 fl. Oz. per acre.

| | Ken Blue Injury | | | | KB Quality | KB Density |
|---|---|---|---|---|---|---|
| | Jul-5 | Jul-12 | Jul-26 | Aug-9 | Jul-16 | Jul-16 |
| Days After Applic. | 8 | 15 | 29 | 43 | 19 | 19 |
| PA-1010 | 0.0 | 0.3 | 0.0 | 0.0 | 8.50 | 8.75 |
| Untreated | 0.3 | 1.0 | 1.3 | 0.5 | 7.75 | 7.75 |

Kentucky bluegrass injury was rated on a scale of 0-10 with 0=none and 10=dead turf. Kentucky bluegrass quality was rated on a scale of 1-9 where, 1=low and 9=high quality. Kentucky bluegrass density was rated on a scale of 1-9 where, 1=open, 6=typical normal density and 9=very dense. This study experienced record breaking high temperatures during the first 2 weeks of the trial. The first eleven days of the trial had 5 days over 90 and 6 days at or over 100 degrees F. The average high temperature for the first eleven days was 98.5 F! No phytotoxicity was observed and treated plots showed higher quality and density than untreated control.

What is claimed:

1. An emulsifiable concentrate for improved herbicidal protection comprising 10 weight percent to 30 weight percent of Prodiamine active herbicidal ingredient, a polar aprotic solvent; a fatty acid dialkylamide solvent; an alkyl based EO(ethylene oxide)-block copolymer emulsifier; an ethoxylated fatty alcohol hydrophilic non-ionic emulsifier; and an anionic emulsifier, wherein the prodiamine is the only active herbicidal ingredient.

2. The formulation of claim 1, comprising 30 weight percent to 60 weight percent of a fatty acid dialkylamide solvent and 10 weight percent to 30 weight percent of a polar aprotic organic solvent.

3. The formulation of claim 2, wherein the fatty acid dialkylamide solvent is dimethylcaprylamide.

4. The formulation of claim 2, wherein the polar aprotic organic solvent is selected from a pyrrolidone, dimethylsulfoxide, dimethylformamide, gamma-Butyrolactone, and mixtures thereof.

5. The formulation of claim 2, comprising 5 weight percent to 8 weight percent of the alkyl based block copolymer emulsifier.

6. The formulation of claim 5, wherein the alkyl based block copolymer emulsifier is an EO-PO butyl block copolymer.

7. The formulation of claim 2, comprising 2 weight percent to 5 weight percent of an ethoxylated trialkyl alcohol as the hydrophilic non-ionic emulsifier.

8. The formulation of claim 1, comprising 20 to about 50 weight percent of N-methylpyrrolidinone, dimethylsulfoxide, dimethylformamide, gamma-Butyrolactone, and mixtures thereof.

9. The formulation of claim 1, wherein the anionic emulsifier comprises an alkyl sulfonate or an alkyl aryl sulfonate.

10. The formulation of claim 1, wherein the formulation contains no N-methylpyrrolidinone, dimethylsulfoxide, dimethylformamide, or gamma-Butyrolactone.

11. A method of use of the formulation of claim 1 when mixed with water and applied to general residential and commercial landscaped areas for effective control of crabgrass, said method comprising mixing an effective amount of the emulsifiable concentrate of claim 1 with water, and applying the mixture to turf.

12. A method of use of the formulation of claim 9 when mixed with water and applied to general residential and commercial landscaped areas for effective control of crabgrass, said method comprising mixing an effective amount of the emulsifiable concentrate of claim 1 with water, and applying the mixture to turf.

13. An emulsifiable concentrate for improved herbicidal protection comprising: a) 10 weight percent to 40 weight percent of prodiamine active herbicidal ingredient; (b) 5 weight percent to 50 weight percent of a polar aprotic organic solvent; (c) 1 weight percent to 12 weight percent of an alkyl based EO(ethylene oxide)-block copolymer emulsifier; and (d) 0.5 weight percent to 5 weight percent of an ethoxylated fatty alcohol hydrophilic non-ionic emulsifier, wherein the prodiamine is the only active herbicidal ingredient.

14. The formulation of claim 13, wherein the polar aprotic organic solvent is selected from a N-methylpyrrolidone, dimethylsulfoxide, dimethylformamide, gamma-Butyrolactone, and mixtures thereof.

15. The formulation of claim 13, wherein the polar aprotic organic solvent consists essentially of N-methylpyrrolidone.

16. The formulation of claim 13 comprising greater than 20% active prodiamine.

17. The formulation of claim 13 comprising 15 weight percent to 20 weight percent of Prodiamine.

18. The formulation of claim 13 comprising 25 to about 35 weight percent of N-methylpyrrolidinone.

19. The formulation of claim 13 further comprising a fatty acid dialkylamide solvent.

20. The emulsifiable concentrate of claim 13, said concentrate consisting essentially of: a) 10 weight percent to 40 weight percent of prodiamine active herbicidal ingredient; (b) 5 weight percent to 50 weight percent of the polar aprotic organic solvent; (c) 1 weight percent to 12 weight percent of the alkyl-alkoxylate-based emulsifier; and (d) 0.5 weight percent to 5 weight percent of the hydrophilic non-ionic emulsifier.

* * * * *